US005720935A

United States Patent [19]
Kassis et al.

[11] Patent Number: 5,720,935
[45] Date of Patent: Feb. 24, 1998

[54] RAPID SYNTHESIS OF RADIOLABELED PYRIMIDINE NUCLEOSIDES OR NUCLEOTIDES FROM STANNYL PRECURSORS

[75] Inventors: Amin L. Kassis, Chestnut Hill; Catherine F. Foulon, Brookline; S. James Adelstein, Waban, all of Mass.

[73] Assignee: President & Fellows of Harvard College, Cambridge, Mass.

[21] Appl. No.: 489,298

[22] Filed: Jun. 9, 1995

[51] Int. Cl.⁶ .................... A61K 51/00; A61M 36/14
[52] U.S. Cl. .................... 424/1.73; 424/1.11; 424/1.65; 536/1.11
[58] Field of Search .................... 424/1.11, 1.65, 424/1.73, 9.1, 1.69; 206/223, 569, 570; 536/1.11, 26.1, 27.1

[56] References Cited

U.S. PATENT DOCUMENTS

| | | | |
|---|---|---|---|
| 3,817,978 | 6/1974 | Jenkins et al. | 536/27.11 |
| 4,321,366 | 3/1982 | Bobek et al. | 536/27.11 |
| 4,851,520 | 7/1989 | Kassis et al. | 536/29 |
| 5,077,034 | 12/1991 | Kassis et al. | 424/1.1 |
| 5,094,835 | 3/1992 | Kassis et al. | 424/1.1 |
| 5,308,605 | 5/1994 | Kassis et al. | 424/1.1 |
| 5,468,853 | 11/1995 | Baranowski-Kortylewicz | 536/28.55 |

OTHER PUBLICATIONS

Journal of Labelled Compounds and Radiopharmaceuticals, vol. XXXIV, No. 6, pp. 513–521 (1994).

*Primary Examiner*—John Kight
*Assistant Examiner*—Dameron Jones
*Attorney, Agent, or Firm*—Sewall P. Bronstein; George W. Neuner

[57] ABSTRACT

A method of making a radiolabeled pyrimidine nucleoside or nucleotide is described. In the method, a stannylated pyrimidine nucleoside or nucleotide is contacted in an aqueous solution with a radioactive iodide, bromide, chlorine or astatine ion in the presence of an acidic hydrogen peroxide oxidizing solution comprising at least a 3:1 ratio of 30% hydrogen peroxide to 1N acid (v/v), whereby a water soluble pyrimidine nucleoside or nucleotide labeled with radioactive iodine, bromine, chlorine or astatine is formed. Kits suitable for practicing the method are also disclosed.

19 Claims, 3 Drawing Sheets

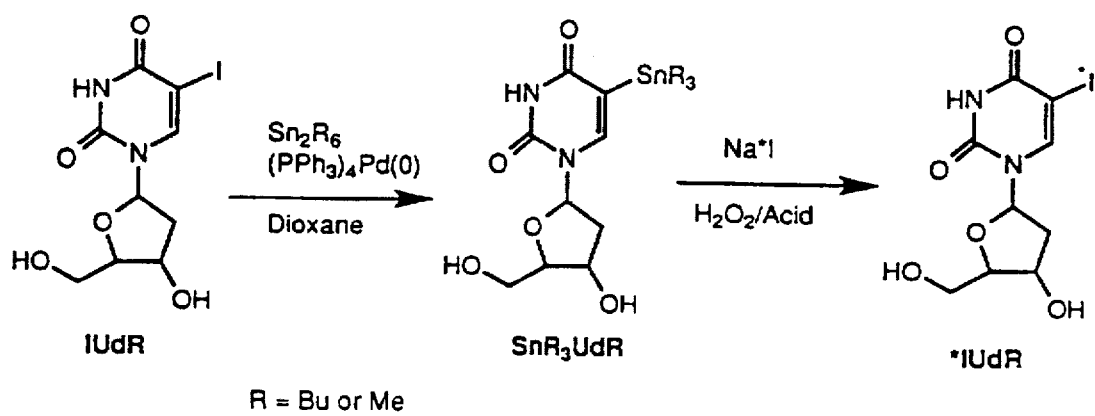
Fig 1: Synthetic route for radiolabeled IUdR

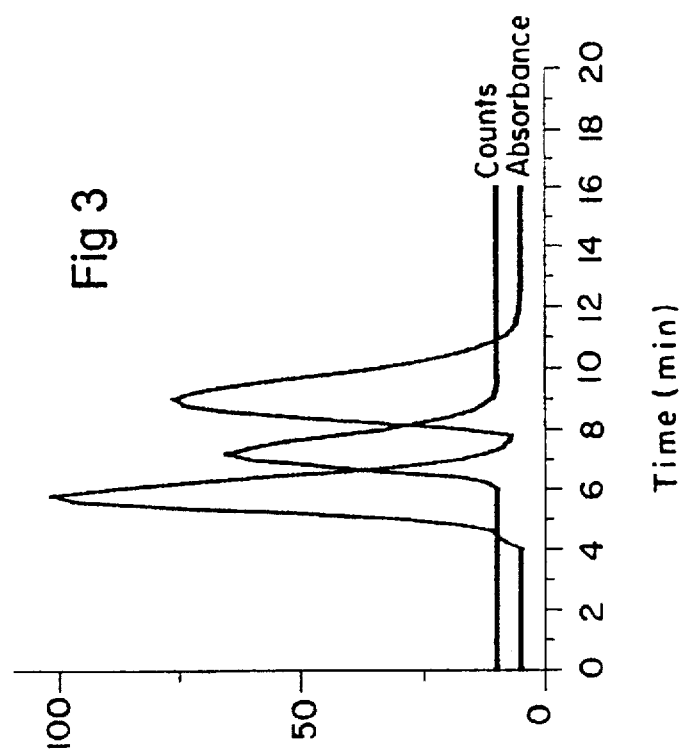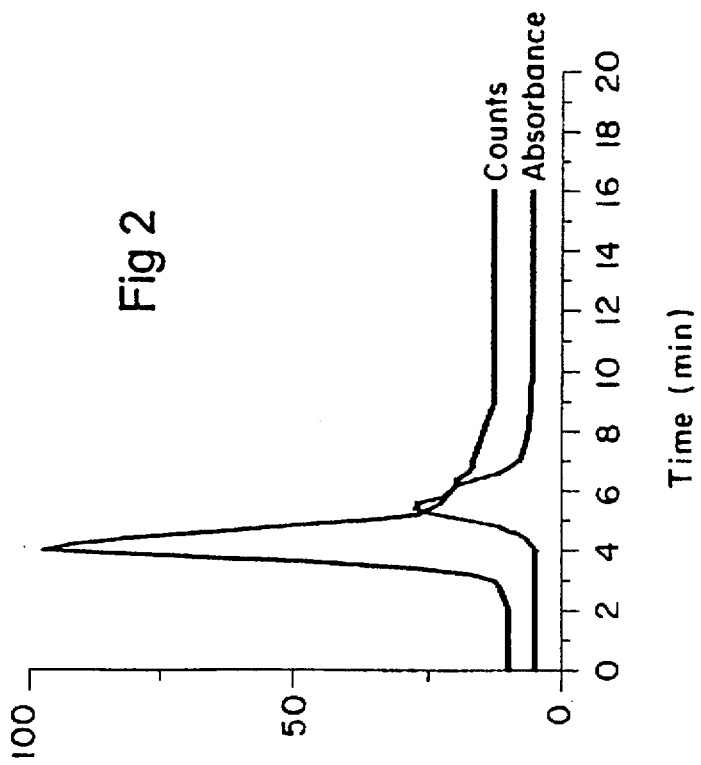

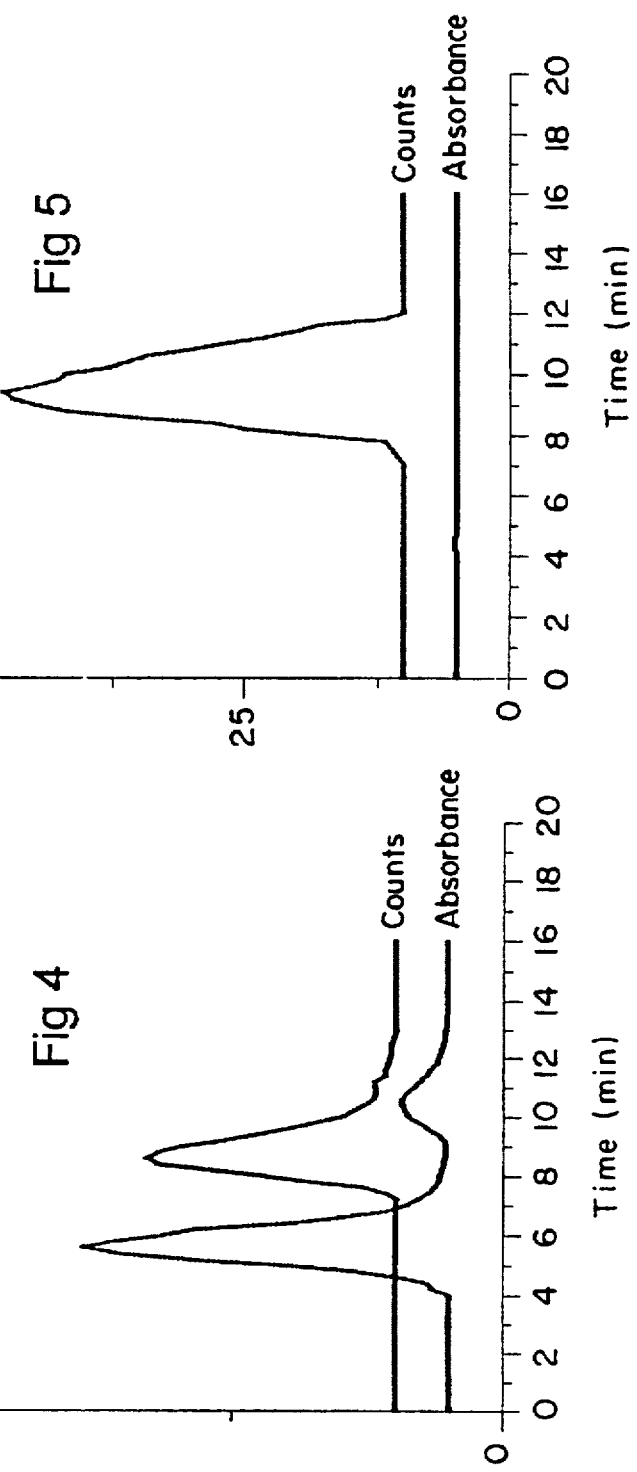

RAPID SYNTHESIS OF RADIOLABELED PYRIMIDINE NUCLEOSIDES OR NUCLEOTIDES FROM STANNYL PRECURSORS

This invention was supported by NIH Grant No. CA15523 and the government has certain rights to the invention.

FIELD OF INVENTION

This invention relates to methods for making radiolabeled pyrimidine nucleosides and nucleotides and, more specifically, to a fast method for labeling with radioactive iodine, bromine, chlorine or astatine, particularly by destannylation of a stannyl precursor.

BACKGROUND OF THE INVENTION

Radiohalogenated pyrimidine nucleosides have been shown to be useful in the diagnosis and treatment of tumors in mammals. For instance, a method of diagnosing tumors using radiohalogenated pyrimidine nucleosides, such as 5-($^{123}$I)Iodo-2'deoxyuridine is described in U.S. Pat. No. 5,094,835 and U.S. Pat. No. 5,308,605, the disclosures of which are incorporated herein by reference. Such radiolabeled compounds can be used to follow the development of tumors. Additionally, tumors in mammals can be treated by injecting or infusing an effective amount of radiohalogenated pyrimidine nucleosides directly to the affected site (see U.S. Pat. No. 5,077,034, the disclosure of which is incorporated herein by reference).

5'-Iodo-2'deoxyuridine (IUdR) is a thymidine (TdR) analog in which the 5-methyl group of TdR is replaced by iodine. Because the 5-methyl group and the iodine atom have similar van der Waals' radii, this substitution gives a compound that behaves remarkably like TdR and, thus, has been extensively studied. Within the cell, both TdR and IUdR are phosphorylated in a stepwise fashion and are incorporated into DNA. Previous studies have shown that this halogenated nucleotide sensitizes mammalian cells to the effects of radiation. When labeled with the Auger electron emitter $^{123}$I or $^{125}$I, radioiodinated IUdR exhibits substantial toxicity in mammalian cells in vitro (Hofer, K. G., et al., (1975) *Int. J. Radiat. Biol.* 28: 225–241; Chan, P. C., et al., (1976) *Radiat. Res.* 67: 332–343; Kassis, A. I., et al., (1987) *Radiat. Res.* 111: 305–318; Makrigiorgos, G. M., et al., (1989) *Radiat. Res.* 118: 532–544) and is highly therapeutic in several animal tumor models (Bloomer, W. D. and Adelstein, S. J. (1977) *Nature* 265: 620–621; Baranowska-Kortylewicz, J., et al., (1991) *Int. J. Radiat. Oncol. Biol. Phys.* 21: 1541–1551; Kassis, A. I., et al., (1993) *J. Nucl. Med.* 34: 241P). Furthermore, the locoregional (intratumoral, intrathecal, intraperitoneal, intravesical) administration of IUdR radiolabeled with the gamma emitter $^{123}$I or $^{131}$I is useful for scintigraphic detection of animal and human tumors (Kassis, A. I., (1990) *J. Nucl. Med. Allied Sci.* 34: 299–303; Kassis, A. I., (1990) *Cancer Res.* 50: 5199–5203; Baranowska-Kortylewicz, J., et al., (1991) supra; Van den Abbeele, A. D., et al., (1992) in *Biophysical Aspects of Auger Processes*, American Association of Physicists in Medicine Symposium Proceedings No 8 (Edited by Howell R. W., Narra V. R., Sastry K. S. R. and Rao D. V.) pp. 372–395, American Institute of Physics, Woodbury, N.Y.; Mariani, G., et al., (1993) *J. Nucl. Med.* 34: 1175–1183; Kassis, A. I., et al., (1994) *Proc. Am. Assoc. Cancer Res.* 35: 414). In addition, intravenously administered radiolabeled IUdR is used in the detection of actively growing regions within tumors (Tjuvajev, J. G., et al., (1994) *J. Nucl. Med.* 35: 1407–1417).

IUdR has certain characteristics which make radiolabeled IUdR useful for the treatment or diagnosis of tumors whether macroscopically observable or not. For instance, since IUdR is a low-molecular-weight molecule, it diffuses readily within tissues. When radiolabeled with an Auger electron emitter, e.g., $^{123}$I, $^{125}$I, $^{77}$Br, $^{80m}$Br, IUdR is innocuous outside the cell and ineffective at killing cells when within the cytoplasm. It is, for the most part, taken up selectively by dividing cancerous cells located within nondividing cells and is indefinitely retained following DNA incorporation. Nondividing cells will not incorporate IUdR into their DNA and most of the IUdR that is not taken up by cancerous cells will be catabolized/dehalogenated rapidly [$t_{1/2}$ of min] and thus will not incorporate into the DNA of distant noncancerous dividing cells. Furthermore, since it is a small molecule, IUdR will not induce an antibody response and as such will lend itself to repeated injections/continuous infusion.

Previously described methods for synthesizing radiolabeled IUdR used a demercurization reaction from a suspension of 5-chloromercuri-2'-deoxyuridine (ClHgUdR) in water using sodium [$^{123/125/131}$I] iodine and Iodogen as the oxidant. The IUdR is isolated and, then, purified by HPLC (high performance liquid chromatography) due to the presence of contaminants, such as UdR, ClUdR and mercury. The entire process typically takes approximately 6 hours (Kassis and Baranowska-Kortylewicz, U.S. Pat. No. 4,851,520; Baranowska-Kortylewicz, J., et al., (1988) *Appl. Radiat. Isot.* 39: 335–341).

Recently, the preparation of radiolabeled IUdR by destannylation of 5-trimethylstannyl-2'-deoxyuridine (($CH_3$)$_3$ SnUdR) has also been described (Baranowska-Kortylewicz, J., et al., (1994) *J. Labelled Cmpd. Radiopharm.* 34: 513–521). Because tin is less toxic than mercury, a trialkylstannyl precursor (e.g., Me$_3$SnUdR or Bu$_3$SnUdR; Me=methyl, Bu=butyl) is attractive as a radiolabeling precursor. Additionally, the stannyl precursor is more stable than the mercurial precursor. These authors claim in the aforementioned publication that, as a consequence of the difference in solubility of the stannyl precursor and IUdR in aqueous solution, radiolabeled IUdR can be isolated by elution through a reverse-phase C$_{18}$ cartridge. However, we have been unable to reproduce these reported results. In fact, IUdR cannot be synthesized from ($CH_3$)$_3$ SnUdR precursor using the conditions prescribed in this publication. Furthermore, contrary to this publication, IUdR cannot be eluted from reverse planar C-18 adsorbents.

It can be appreciated that it is desirable to have a method for synthetic preparation of radiolabeled pyrimidine nucleosides or nucleotides that is rapid, efficient, and easily reproducible. It is further desirable that such a process produces radiolabeled nucleosides or nucleotides free of toxic contaminants and which therefore do not require further purification.

SUMMARY OF THE INVENTION

The radiolabeling conditions of trialkyllstannyl nucleosides and nucleotides have been studied using UdR as a model compound to identify the reaction conditions that lead to the rapid production of no-carrier-added radioiodinated nucleosides and nucleotides, the sample being void of all UV-contaminating species. Thus, the method of this invention enables the production of no-carrier-added radiolabeled nucleosides or nucleotides such as radiohalogenated deoxyuridine, without UV-contaminating species such as tin precursors, e.g., trialkylstannyl UdR, etc. The present invention provides a method for the rapid synthesis of radiolabeled (e.g. $^{123}$I, $^{124}$I, $^{125}$I, $^{131}$I, $^{75}$Br, $^{76}$Br, $^{77}$Br, $^{80}$Br, $^{80m}$Br and $^{211}$At) nucleosides and nucleotides for biological or clinical use.

The method of the present invention comprises adding a radioactive halide, particularly iodide, bromide or astatide, to a solution containing a trialkylstannylated nucleoside or nucleotide precursor, in the presence of an oxidative solution. The oxidative solution comprises an acidic solution of hydrogen peroxide ($H_2O_2$). Preferably, the oxidative solution comprises $H_2O^2$ and an acid in a ratio of at least three parts 30% hydrogen peroxide solution to one part 1N acid (v/v).

In a further embodiment, the present invention provides a kit for the production of radiolabeled nucleosides or nucleotides. The kit comprises a premeasured amount of a trialkylstannylated nucleoside or nucleotide precursor, such as for example, 5-trimethylstannyl-2'-deoxyuridine or 5-tributylstannyl-2'-deoxyuridine in a sterilized container and a premeasured amount of the oxidative solution in a second sterilized container. In a preferred embodiment, the precursor, e.g., $Bu_3SnUdR$, is complexed with a carrier molecule, e.g., bound to the surface of beads or a test tube. Such kits are particularly useful for clinical applications.

At room temperature, the reaction replacing tin with radioactive iodide, bromide or astatide, according to the method of this invention can be completed in less than about 1 min. The invention will be described in detail by exemplification using 2'-deoxyuridine. However, those skilled in the art will readily appreciate that the methods are equally useful for other nucleosides and nucleotides.

BRIEF DESCRIPTION OF THE DRAWINGS

FIG. 1 shows the synthetic route for preparation of radioiodinated IUdR via triakylstannyl precursors.

FIG. 2 is an HPLC chromatogram of reaction products from radiosynthesis of IUdR using $Me_3SnUdR$ precursor and 5 µL oxidant solution in accord with the procedure described by Baranowska-Kortylewicz et al. (1994), supra.

FIG. 3 is an HPLC chromatogram of reaction products from radiosynthesis of IUdR using 100 µg $Me_3SnUdR$ precursor and 100 µL oxidant solution.

FIG. 4 is an HPLC chromatogram of reaction products from radiosynthesis of IUdR using 100 µg $Bu_3SnUdR$ precursor and 100 µL oxidant solution.

FIG. 5 is an HPLC chromatogram of reaction products from radiosynthesis of IUdR with 10 µg $Bu_3SnUdR$ precursor and 30% hydrogen peroxide:1N HCl 4/1 diluted at 1/10,000 in accord with a preferred embodiment of the present invention.

DETAILED DESCRIPTION OF THE INVENTION

Previously known methods for the synthesis of radiolabeled pyrimidine nucleosides, such as IUdR, typically have been limited by long preparation times, low yield, and contaminating UV species. The preparation of radiolabeled 5-iodo-2'-deoxyuridine (IUdR) by iododemetallation has been reported in the literature, either by demercuration of ClHgUdR (Baranowska-Kortylewicz et al., (1988) *Appl. Radiat. Isot.* 39: 335–341) or by destannylation of $Me_3SnUdR$ (Baranowska-Kortylewicz et al., (1994) supra). Because of the lesser toxicity of tin compared with mercury, we have investigated the radiolabeling conditions of the trialkylstannyl precursor ($Me_3SnUdR$ or $Bu_3SnUdR$). However, efforts to reproduce the procedure described by Baranowska-Kortylewicz et al. (1994) were fruitless in that no radiolabeled IUdR could be synthesized (FIG. 2). Even under conditions which were determined by us to provide an exchange, although the exchange of the iodide/trialkylstannyl was complete at the time, several undesirable UV-absorbing by-products were detected (FIGS. 3,4).

In accord with the present invention, a method of making a radiolabeled pyrimidine nucleoside or nucleotide is provided which comprises contacting a trialkylstannylated precursor with a radioactive ion in an oxidative solution. The oxidative solution comprises an acidic solution of hydrogen peroxide ($H_2O_2$). Preferably, the oxidative solution comprises $H_2O_2$ and an acid in a ratio of at least three parts 30% hydrogen peroxide solution to one part 1N acid (v/v). In a preferred embodiment, the oxidative solution is diluted at least 1 part per 10,000 parts water. In a preferred embodiment, the final radiolabeled product is available within about 5 min in quantitative yield and does not require purification.

For attempts to conduct the iododestannylation to produce IUdR in accord with prior art methods, trimethyl- and tributylstannyl derivatives of IUdR were synthesized in good yield (Wigerinck et al., *Med. Chem.* 36, p.538–43 1993), but efforts to reproduce radiolabeling under the conditions described by Baranowska-Kortylewicz et al. (1994) were unsuccessful (FIG. 1). First, when 5 µL oxidative solution (hydrogen peroxide/acetic acid, 1:3 ratio (v/v)) is used, the reaction which replaces the tin with the radioactive halide does not take place and the HPLC chromatograms (FIG. 2) display only a radioactive peak corresponding to radioactive iodine (4 min) and a UV peak corresponding to UdR (5 min). Second, it is difficult to elute [$^{125}$I] UdR from the $C_{18}$ cartridge following the methods of this reference which uses water, 0.9% sodium chloride, or phosphate buffer. Finally, when we determined that exchange can be accomplished by using 100 µL oxidative solution (hydrogen peroxide/acetic acid, 1:3 ratio (v/v)) and such samples were injected into the HPLC to ascertain the quality of the final product, two UV-absorbing species, UdR (5 min) and an unidentified product co-eluting with IUdR (FIG. 3), were present in addition to the quantitative exchange of sodium iodide to produce IUdR. Similarly, UV-absorbing species were also present when the tributylstannyl derivative was used as a precursor in the synthesis (FIG. 4). In such preparations, an insignificant quantity of tin (<0.06 ppm, water=0.06 ppm) was found in the final radiolabeled IUdR preparations.

The methods of the present invention provide a quick and efficient method of producing radiolabeled pyrimidine nucleosides and nucleotides free from contaminants for biological or clinical use. A stannylated precursor is provided. In a preferred embodiment of the invention, the precursor is selected from the trimethylstannyl analogue or tributylstannyl analogue. Most preferably, the precursor comprises the tributylstannyl group because of the lesser toxicity of the tributylstannyl group compared with the trimethylstannyl group.

The methods of the present invention can be applied to any trialkylstannyl-pyrimidine nucleoside such as 5-trialkylstannyl-cytidine, 5-trialkylstannyl-2'-deoxycytidine, 5-trialkylstannyl-uridine, 5-trialkylstannyl-2'-deoxyuridine, or to any trialkylstannyl-pyrimidine nucleotide such as 5-trialkylstannyl-cytidine-5-mono-, di, or triphosphate, 5-trialkylstannyl-uridine-5'-mono-, di-, or triphosphate, or 5-trialkylstannyl-2'-deoxyuridine-5'-mono-, di-, or tri-phosphate.

The trimethylstannyl derivative of IUdR, for example, can be synthesized in good yield by the methods described by Wigerinck et al., supra. Precursor analogues of other nucleosides and nucleotides can be made be similar procedures. Tributylstannyl UdR ($Bu_3SnUdR$) also can be prepared by the action of bis(tributyltin) on IUdR in the presence of palladium (0) catalyst (FIG. 1). It can be purified by column chromatography and obtained in good yield as a yellow oil. The tributylstannyl precursor is preferred because it enables better separation between the tributylstannyl derivative and the UdR (main by-product of the reaction) by column chromatography than the trimethylstannyl precursor. Residual IUdR would decrease the specific activity of the final preparation of radiolabeled IUdR.

For the purposes of illustration, the 5-tributylstannyl-2'deoxyuridine nucleoside ($Bu_3SnUdR$) will be referred to in detail as an example to demonstrate the present invention. It should be understood, however, that such exemplification does not limit the invention described herein to this nucleoside.

For the radiolabel, a radioactive iodine, bromine, chlorine or astatine ion can be employed in the form of any water-soluble salt, e.g., an alkali metal salt such as the sodium salt of a radioactive halide, for example, $^{123}I$, $^{124}I$, $^{125}I$, $^{126}I$, $^{128}I$, $^{129}I$, $^{130}I$, $^{131}I$, $^{132}I$, $^{133}I$, $^{134}I$, $^{135}I$, $^{74}Br$, $^{75}Br$, $^{76}Br$, $^{77}Br$, $^{80}Br$, $^{80m}Br$, $^{82m}Br$, $^{83}Br$, $^{84}Br$, $^{34m}Cl$, $^{38}Cl$, $^{38m}Cl$, $^{39}Cl$ or $^{211}At$, preferably in carrier-free form. The concentration of iodide, bromide, chlorine or astatide ion in the aqueous reaction medium can range from 0.1 mCi/mL to 1000 mCi/mL, preferably from 0.1 mCi/mL to 100 mCi/mL. Commercial radioactive sodium iodide is provided at pH 7–11. It is preferable to neutralize the pH of the radiolabel solution prior to use, for example, with 0.1N HCl.

The oxidizing solution, in accord with the present invention, requires hydrogen peroxide and an acid in a predetermined ratio to effect destannylation while decreasing the formation of UV-absorbing by-products such as UdR and ClUdR. For convenience, an aqueous 30% hydrogen peroxide solution and 1N acid will be used to define the ratio of hydrogen peroxide to acid for an oxidizing solution of the present invention. The ratio of 30% hydrogen peroxide to 1N acid should be at least 3:1, preferably at least 4:1. The exchange iodide/tributyltin is quantitative.

Preferably, when using a stock oxidizing solution prepared from a ratio of 30% hydrogen peroxide and 1N acid (e.g., 4/1 ratio), the resulting oxidizing solution is further diluted. The preferred dilution of the stock oxidizing solution is at least 1 part oxidizing solution to 1000 parts water, more preferably to at least 10,000 parts water. Chromatograms clearly show the progressive reduction of UV-absorbing by-products (i.e. UdR at 5 min and unidentified product at 7 min) with the decrease of acid content. In all cases, the exchange of iodide/tin is complete (FIG. 5).

The acid used in the practice of the present invention can be chosen from a variety of acids. Examples of suitable acids are acetic acid and HCl, which are pharmacologically acceptable. Because hydrodestannylation occurs rapidly, it is preferable to delay contact between the acid and the stannylated precursor. As such, preparation of the acidic oxidative solution separately and in advance is preferred.

Because of the ease of the procedure and the rapid synthesis involved, the method of this invention is suitable for kit formulation. This invention provides for a kit in which a desired radionucleotide, e.g., $^{125}IUdR$, is prepared according to the method described herein and is contained in a pharmaceutically acceptable vehicle such as sterile normal saline yielding an effective diagnostic or therapeutic amount per dose unit. Generally speaking, each dose contains about 1–25 mCi (diagnosis) and 10–5000 mCi (therapy) of the selected radioactive compound. The pharmaceutically acceptable compositions for administration of the radiolabeled nucleoside or nucleotide can be formulated by methods known to those ordinarily skilled in pharmacology, using suitable non-toxic parenterally acceptable diluents such as normal saline, Ringer's solution, and formulating into sterile dosage forms for those administrations.

Thus, the present invention further comprises easy to use kits providing a stannylated precursor that can be readily radiolabeled with the desired nuclear label. Such a kit, in accord with the present invention, comprises a sterilized, non-pyrogenic container containing the stannylated precursor. The tin precursor is soluble in organic solvents such as ethyl acetate, chloroform, and methanol and, thus, can be coated on the walls of containers, such as centrifuge vials. It is preferred that the precursor, e.g., $Bu_3SnUdR$, is present in an amount of 10 to 500 µg. Preferred kits contain about 10 µg or about 100 µg of stannylated precursor. The kit further comprises a sterilized, non-pyrogenic container containing the oxidative solution. The kit may also contain an apyrogenic sterilizing filter, a syringe and a sterile vial for the convenience of the user.

Preferred kits, in accord with the present invention, comprise a sterilized, non-pyrogenic container containing the water-soluble precursor compound, e.g., $SnBu_3UdR$, and a second sterilized, non-pyrogenic container containing the oxidizing solution. It is preferred that $SnBu_3UdR$ be present in the container or test tube in about 10 µg or 100 µg. Preferably, the container is a test tube, the wall of which is coated with the $SnBu_3UdR$. The oxidizing solution preferably is present in the diluted form so that it can be added to the precursor without further preparation. The kit may also contain a 0.22 µm filter, a chelating disc, 0.1N HCl, a sterile vial, and a syringe for the convenience of the user.

Preferably, the kit contains an apyrogenic sterilizing filter adjacent to an ion exchange membrane on which is immobilized a premeasured amount of a water soluble pyrimidine nucleoside or nucleotide precursor. The kit can be conveniently formed in a filter pack having the apyrogenic sterilizing filter and the ion exchange membrane stacked sequentially. A solution containing the radioactive label and the oxidant can be injected through the pack to form the radiolabeled nucleoside or nucleotide in a sterile form.

It is to be understood that the specific dose level and the particular dosage regimen for any particular patient will depend upon a variety of factors including for example, the age, body weight, sex and severity of the particular condition of the host undergoing therapy. The dosage regimen therefore needs to be individualized by the clinician based on clinical response.

The following specific examples are intended to illustrate more fully the nature of the invention without limiting its scope.

EXAMPLE 1

Preparation of 5-Tributylstannyl-2'-deoxyuridine ($Bu_3SnUdR$)

IUdR (1.41 mmol, 500 mg) was dissolved in 1,4-dioxane (20 mL) while the flask was maintained at 50° C. After cooling to room temperature, bis(tributyltin) (3.1 mmol, 1.6 mL) and tetrakis(triphenylphosphine)palladium(0) (0.04 mmol, 50 mg) were added and the mixture heated at 105° C. overnight under a stream of nitrogen. The solvent was removed by rotary evaporation, and the dark mixture was subjected to flash-chromatography (silica gel, chloroform:methanol, 80/20) and TLC (chloroform:methanol, 92/8). The desired product ($R_f$=0.23) was obtained as a pale yellow oil (584.1 mg, 80%). $^1$H-NMR ($CDCl_3$): 7.51 (s, 1H, CH6); 6.38 (t,1H, CHP1'); 4.84 (m, 1H, CH3'); 4.29 (m, 1H, CH4'); 4.09 (s, 2H, CH5'); 3.73 (s, 1H, OH3'); 3.39 (s, 1H, OH5'); 2.29 (m, 2H, CH2'); 1.97–1.57 (m, 27H, 3nBu).

Samples of 100 μg or 10 μg $Bu_3SnUdR$ are preferably aliquoted and kept in the freezer until use. The stability of the precursor can be monitored by HPLC. $Bu_3SnUdR$ (100 μg), mixed with 100 μL water, is injected into HPLC. The column is first eluted with water:methanol, 80/20, at 1 mL/min flow-rate and no UV-absorbing product should be detected at the sensitivity 0.05/50 mV. When the mobile phase is switched to methanol, the precursor is eluted 14 min later. If any by-products are detected during the first elution, the precursor should be repurified by preparative TLC (chloroform:methanol, 92/8).

EXAMPLE 2

Preparation of 5-[$^{125}$I] Iodo-2'-deoxyuridine ($^{125}$IUdR)

5 μL of 30% hydrogen peroxide: 1N HCl (4:1, v/v), diluted 1/10,000 in sterile water, was added to a 300-μL vial coated with 10 μg 5-tributylstannyl-2'-deoxyuridine ($Bu_3SnUdR$), containing 20 μL water and 1–500 μCi $Na^{125}I$. The vial was vortexed for 10 sec and 100 μL saturated aqueous solution of sodium metabisulfite was added. The sample was either injected into HPLC (as a quality control, water:methanol, 80/20, 1 mL/min; Rt=9 min; UV sensitivity=0.05/50 mV) or eluted through a 0.22-μm apyrogenic disk for biological or clinical application. HPLC shows no non-labeled UV-absorbing products (FIG. 5).

EXAMPLE 3

Tin Quantitation

200 μL sodium iodide (7.25 μg/mL in distilled water, titrated to represent 10 mCi of $Na^{131}I$) were added to a vial coated with the stannyl precursor (10 μg) prepared in Example 1, along with 50 μL of 30% hydrogen peroxide/1N HCl:4/1. The vial was vortexed for 10 sec and the volume was completed to 500 μL with distilled water (except for sample 3). The sample (200 μL, except sample 3 which was submitted as such) was sent to Galbraith Laboratories, Knoxville, Tenn., for tin analysis (see table below).

| CONTENT | RESULT |
|---|---|
| 10 μg $Bu_3SnUdR$ in 500 μL water | <0.06 mg/L |
| 10 μg $Bu_3SnUdR$, NaI, oxidant, up to 500 μL water | <0.06 mg/L |
| 10 μg $Bu_3SnUdR$, NaI, oxidant, no water added | 0.09 mg/L |
| water | 0.07 mg/L |

These results demonstrate that the preparation of radiolabeled IUdR does not generate more tin contaminants than are already contained in water.

Although the tin analysis results show that the metal contamination is not an issue in the preparation of IUdR by destannylation, the removal of unreacted metallic precursor is always desirable. Moreover, the reaction preferably should be quenched by sodium metabisulfite at end of the radiolabeling because the oxidant is still present in the mixture and, unless the HPLC shows the complete transformation of iodide into IUdR, there is still the possibility of releasing labile iodonium.

The invention has been described in detail with particular reference to the preferred embodiments thereof. However, it will be appreciated that modifications and improvements within the spirit and scope of this invention may be made by those skilled in the art upon considering the present disclosure.

What is claimed is:

1. A method of making a radiolabeled pyrimidine nucleoside or nucleotide, the method comprising contacting in an aqueous solution (i) a radioactive iodide, bromide, chlorine or astatine ion; (ii) a stannylated pyrimidine nucleoside or nucleotide and (iii) an acidic hydrogen peroxide oxidizing solution comprising at least a 3:1 ratio of 30% hydrogen peroxide to 1N acid (v/v), whereby a water soluble pyrimidine nucleoside or nucleotide labeled with radioactive iodine, bromine, chlorine or astatine is formed.

2. The method as claimed in claim 1, wherein the acidic hydrogen peroxide oxidizing solution is diluted at least one part to 1000 parts water (v/v).

3. The method as claimed in claim 1, wherein the acid is a pharmaceutically acceptable acid.

4. The method as claimed in claim 1, wherein the acid is acetic acid, hydrochloric acid, or nitric acid.

5. The method as claimed in claim 1, wherein the stannylated pyrimidine nucleoside or nucleotide comprises a trimethyl stannyl analogue or a tributylstannyl analogue of a pyrimidine nucleoside or nucleotide.

6. The method as claimed in claim 1, wherein the stannylated pyrimidine nucleoside comprises the tributylstannyl analogue.

7. The method of claim 1, wherein the stannylated pyrimidine nucleoside or nucleotide is immobilized on a solid surface.

8. The method of claim 1, wherein a radioactive iodide ion is used to label the stannylated pyrimidine nucleoside or nucleotide.

9. The method of claim 1, wherein a radioactive bromide ion is used to label the water soluble pyrimidine nucleoside or nucleotide.

10. The method of claim 1, wherein a radioactive astatine ion is used to label the water soluble pyrimidine nucleoside or nucleotide.

11. The method of claim 1, wherein the radioactive ion is added in a acid neutralized solution to label the water soluble pyrimidine nucleoside or nucleotide.

12. A kit suitable for forming a radiolabeled pyrimidine nucleoside or nucleotide, the kit comprising a premeasured amount of a stannylated pyrimidine nucleoside or nucleotide in a first sterile, non-pyrogenic container and an acidic hydrogen peroxide oxidizing solution comprising at least a 3:1 ratio of 30% hydrogen peroxide to 1N acid (v/v) in a second sterile, non-pyrogenic container.

13. The kit of claim 12, containing 5-tributylstannyl-2'-deoxyuridine.

14. The kit of claim 12, containing 5-trimethylstannyl-2'-deoxyuridine.

15. The kit of claim 12, wherein the stannylated pyrimidine nucleoside or nucleotide is immobilized on a solid surface.

16. The kit of claim 15, wherein the solid surface is a glass surface.

17. The kit of claim 12, wherein the oxidizing solution comprises a pharmaceutically acceptable acid.

18. The kit of claim 17, wherein the acid is acetic acid, hydrochloric acid, or nitric acid.

19. The kit of claim 12, further comprising an apyrogenic, sterilizing filter.

* * * * *